(12) United States Patent
Zetina-Rocha et al.

(10) Patent No.: US 8,993,579 B2
(45) Date of Patent: Mar. 31, 2015

(54) POLYMORPHIC FORMS OF LAPATINIB DITOSYLATE AND PROCESSES FOR THEIR PREPARATION

(75) Inventors: Carlos Zetina-Rocha, Brantford (CA); Eduardo Gustavo Cammisa, Oshawa (CA); Gamini Weeratunga, Ancaster (CA)

(73) Assignee: Apotex Pharmachem Inc, Brantford (CA)

( * ) Notice: Subject to any disclaimer, the term of this patent is extended or adjusted under 35 U.S.C. 154(b) by 0 days.

(21) Appl. No.: 13/642,712

(22) PCT Filed: Apr. 21, 2011

(86) PCT No.: PCT/CA2011/000439
§ 371 (c)(1),
(2), (4) Date: Jan. 28, 2013

(87) PCT Pub. No.: WO2011/130831
PCT Pub. Date: Oct. 27, 2011

(65) Prior Publication Data
US 2013/0123497 A1    May 16, 2013

Related U.S. Application Data

(60) Provisional application No. 61/326,838, filed on Apr. 22, 2010.

(51) Int. Cl.
| | | |
|---|---|---|
| A61K 31/517 | (2006.01) | |
| C07D 239/72 | (2006.01) | |
| C07D 405/10 | (2006.01) | |
| C07C 309/30 | (2006.01) | |
| C07D 405/04 | (2006.01) | |
| C07C 303/32 | (2006.01) | |

(52) U.S. Cl.
CPC ............ *C07D 405/10* (2013.01); *C07C 309/30* (2013.01); *C07D 405/04* (2013.01); *C07C 303/32* (2013.01)
USPC ........................................ 514/258.1; 544/293

(58) Field of Classification Search
CPC ...................................................... C07D 405/04
See application file for complete search history.

(56) References Cited

U.S. PATENT DOCUMENTS

2009/0281315 A1* 11/2009 Metsger et al. ............... 544/293

FOREIGN PATENT DOCUMENTS

WO   WO 2009137714 A2 * 11/2009

\* cited by examiner

*Primary Examiner* — Noble Jarrell
*Assistant Examiner* — John S Kenyon (57) ABSTRACT

There is provided a crystalline form of Lapatinib, termed APO-I, and methods for making APO-I. There is also provided a crystalline solvate form of Lapatinib, termed APO-II, and methods for making APO-II.

24 Claims, 4 Drawing Sheets

POLYMORPHIC FORMS OF LAPATINIB DITOSYLATE AND PROCESSES FOR THEIR PREPARATION

TECHNICAL FIELD

The present invention relates to polymorphic forms of Lapatinib ditosylate and processes for their preparation.

BACKGROUND

Lapatinib ditosylate (1) is a kinase inhibitor and is indicated in combination with: (1) capecitabine, for the treatment of patients with advanced or metastatic breast cancer whose tumors overexpress HER2 and who have received prior therapy including an anthracycline, a taxane, and trastuzumab and (2) letrozole for the treatment of postmenopausal women with hormone receptor positive metastatic breast cancer that overexpresses the HER2 receptor for whom hormonal therapy is indicated. It is marketed in USA as Tykerb®. Chemically, Lapatinib ditosylate is N-(3-chloro-4-{[(3-fluorophenyl)methyl]oxy}phenyl)-6-[5-({[2-(methylsulfonyl)ethyl]amino}methyl)-2-furanyl]-4-quinazolinamine bis(4-methylbenzenesulfonate).

Lapatinib Ditosylate

U.S. Pat. No. 6,713,485 relates to substituted heteroaromatic compounds, methods for their preparation, pharmaceutical compositions containing them and their use in medicine. Specifically, U.S. Pat. No. 6,713,485 relates to quinazoline derivatives useful in treating disorders mediated by protein tyrosine kinase activity, in particular erbB-2 and/or EGFR activity.

U.S. Pat. No. 7,157,466 describes ditosylate salts of 4-quinazolineamines as well as methods of using the same in the treatment of disorders characterized by aberrant erbB family PTK activity.

WO 2008/154469 describes salts of 4-quinazolineamines as well as methods of using the same in the treatment of disorders characterized by aberrant erbB family PTK activity.

WO 2009/079541 describes crystalline forms of anhydrate ditosylate salts of 4-quinazolineamines as well as methods of using the same in the treatment of disorders characterized by aberrant erbB family PTK activity.

WO 2009/079547 describes crystalline forms of 4-quinazolineamines as well as methods of using the same in the treatment of disorders characterized by aberrant erbB family PTK activity.

US 2009/0281315 provides polymorphs of Lapatinib ditosylate, processes for preparing them, and pharmaceutical compositions comprising one or more of these polymorphs.

US 2009/0306106 provides crystalline forms of Lapatinib base, Form X and Form Y, and amorphous Lapatinib base, pharmaceutical compositions comprising the crystalline forms of Lapatinib base, and/or the amorphous Lapatinib base, and processes for their preparation.

SUMMARY

The present invention relates, at least in part, to crystalline forms of Lapatinib ditosylate, namely polymorphic forms of Lapatinib ditosylate termed herein APO-I and APO-II. Processes for preparing these forms are also provided.

In illustrative embodiments of the present invention, there is provided APO-I polymorphic form of Lapatinib ditosylate.

In illustrative embodiments of the present invention, there is provided an APO-I polymorphic form of Lapatinib ditosylate described herein having a powder X-ray diffraction pattern comprising peaks, in terms of degrees 2-theta, at approximately 4.6, 18.8, 19.5, 21.3, 22.0 and 23.0.

In illustrative embodiments of the present invention, there is provided an APO-I polymorphic form of Lapatinib ditosylate described herein wherein the powder X-ray diffraction pattern further comprising peaks, in terms of degrees 2-theta, at approximately 8.3, 9.3, 11.8, 13.8, 14.9, 16.8, 17.3, 25.2 and 26.2.

In illustrative embodiments of the present invention, there is provided an APO-I polymorphic form of Lapatinib ditosylate described herein having a DSC thermogram comprising two endothermic peaks with peak onset temperatures of approximately 169.5° C. and 247.9° C. and peak maximums of approximately 179.5° C. and 250.5° C.

Figure 1:
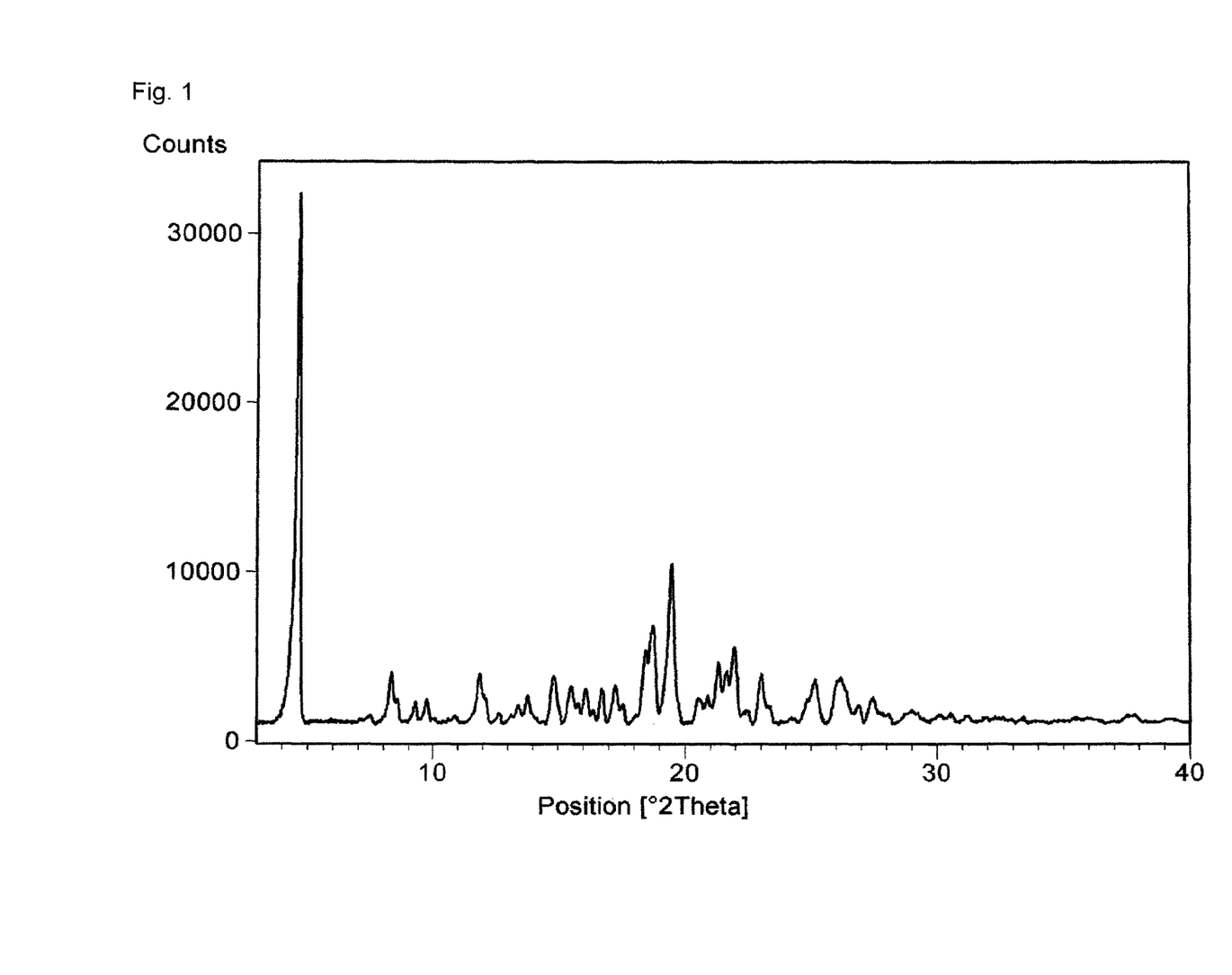
FIG. 1: is a powder X-ray diffraction (PXRD) diffractogram of APO-I.

In illustrative embodiments of the present invention, there is provided an APO-I polymorphic form of Lapatinib ditosylate described herein having a PXRD diffractogram substantially similar to a PXRD diffractogram as depicted in FIG. 1.

Figure 2:
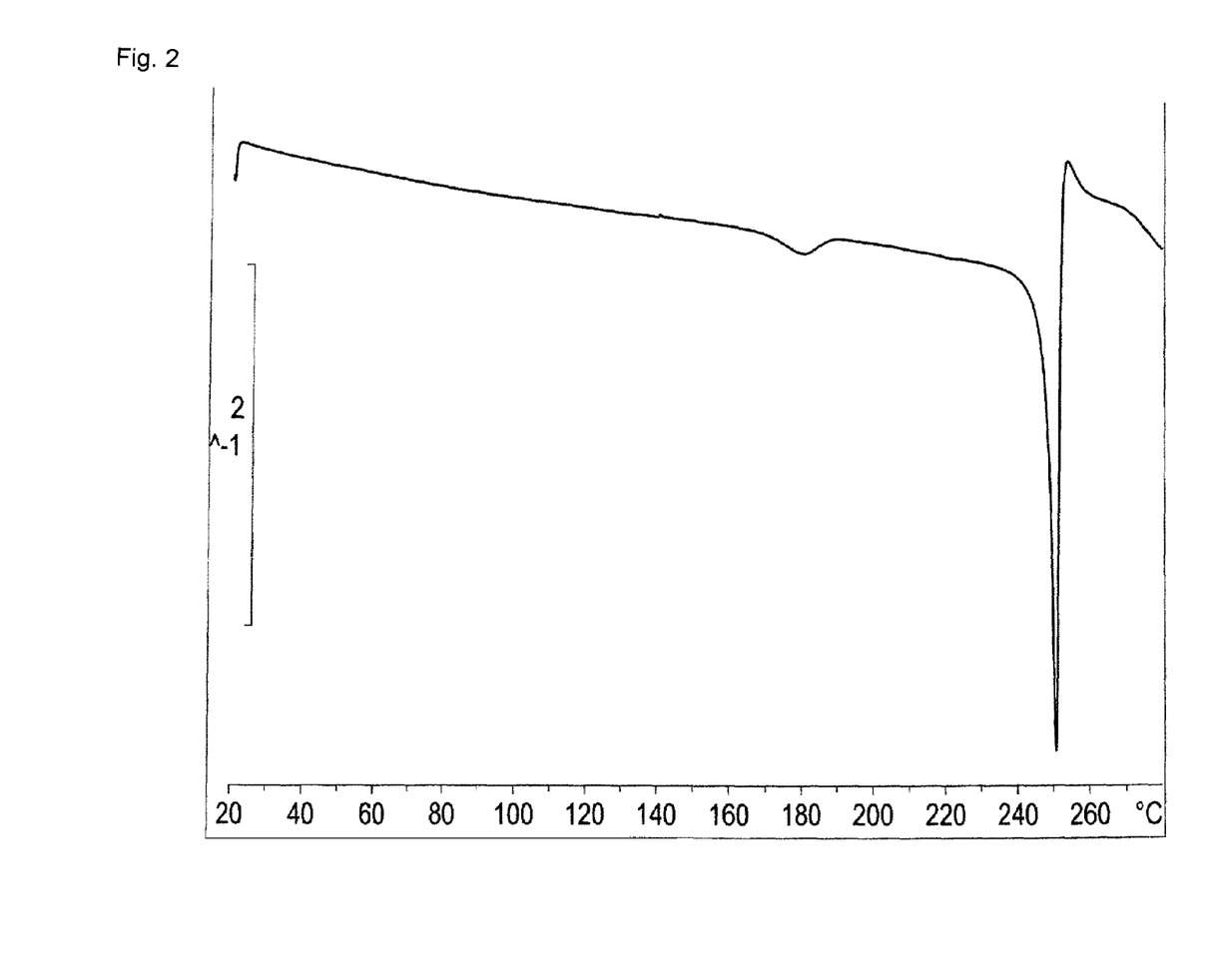
FIG. 2: is a differential scanning calorimetry (DSC) thermogram of APO-I.

In illustrative embodiments of the present invention, there is provided an APO-I polymorphic form of Lapatinib ditosylate described herein having a DSC thermogram substantially similar to a DSC thermogram as depicted in FIG. 2.

In illustrative embodiments of the present invention, there is provided APO-II polymorphic form of Lapatinib ditosylate.

In illustrative embodiments of the present invention, there is provided an APO-II polymorphic form of Lapatinib ditosylate described herein having a powder X-ray diffraction pattern comprising peaks, in terms of degrees 2-theta, at approximately 4.4, 8.3, 13.1, 19.3, 20.9 and 21.4.

In illustrative embodiments of the present invention, there is provided an APO-II polymorphic form of Lapatinib ditosylate described herein wherein the powder X-ray diffraction pattern further comprising peaks, in terms of degrees 2-theta, at approximately 9.6, 10.5, 14.0, 15.0 16.9, 18.2, 25.3, and 26.6.

In illustrative embodiments of the present invention, there is provided an APO-II polymorphic form of Lapatinib ditosylate described herein having a DSC thermogram comprising three endothermic peaks with peak onset temperatures of approximately 98.5° C., 167.7° C. and 247.0° C. and peak maximums of approximately 119.5° C., 177.8° C. and 249.4° C.

Figure 3:
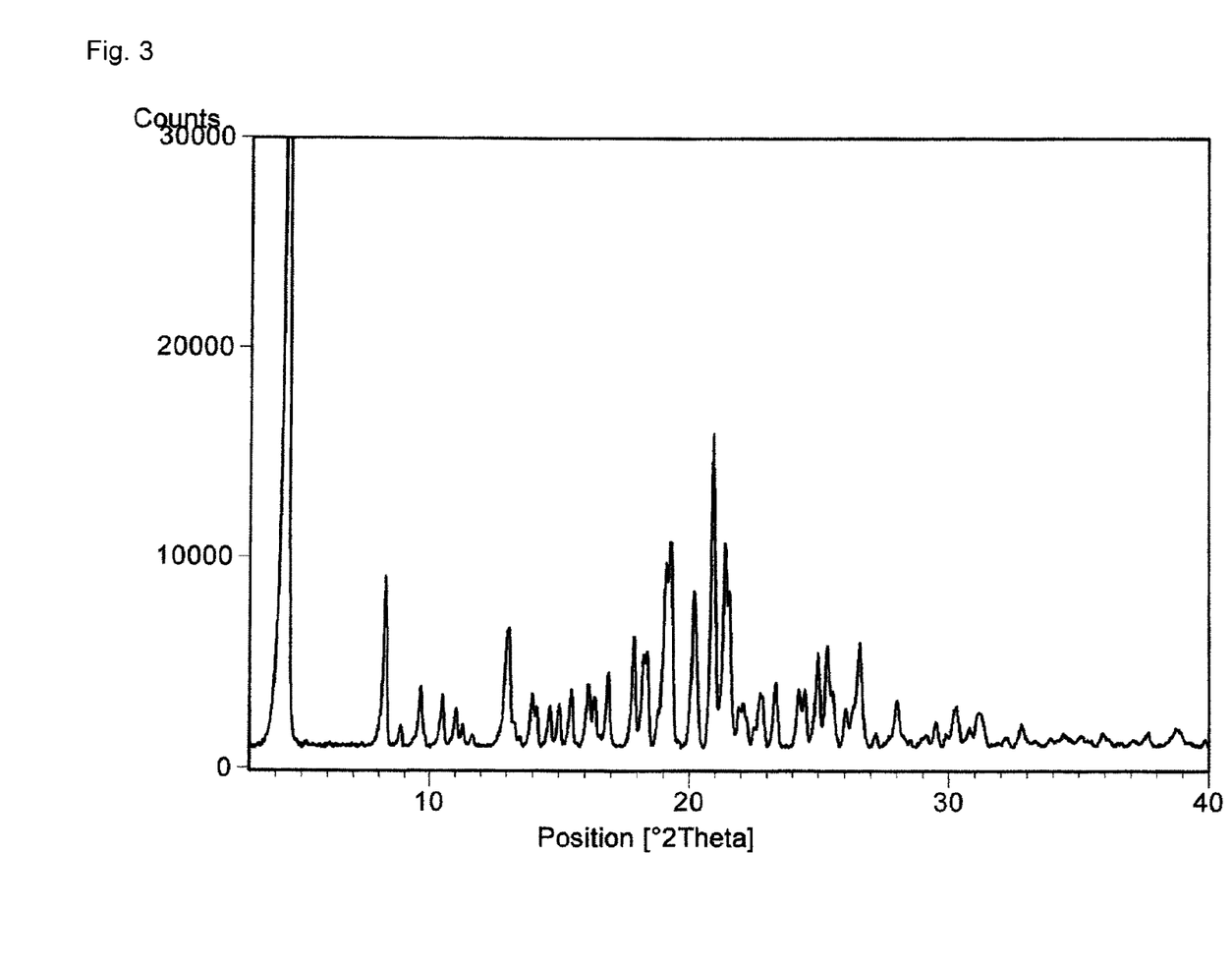
FIG. 3: is a powder X-ray diffraction (PXRD) diffractogram of APO-II.

In illustrative embodiments of the present invention, there is provided an APO-II polymorphic form of Lapatinib ditosylate described herein having a PXRD diffractogram substantially similar to a PXRD diffractogram as depicted in FIG. 3.

Figure 4:
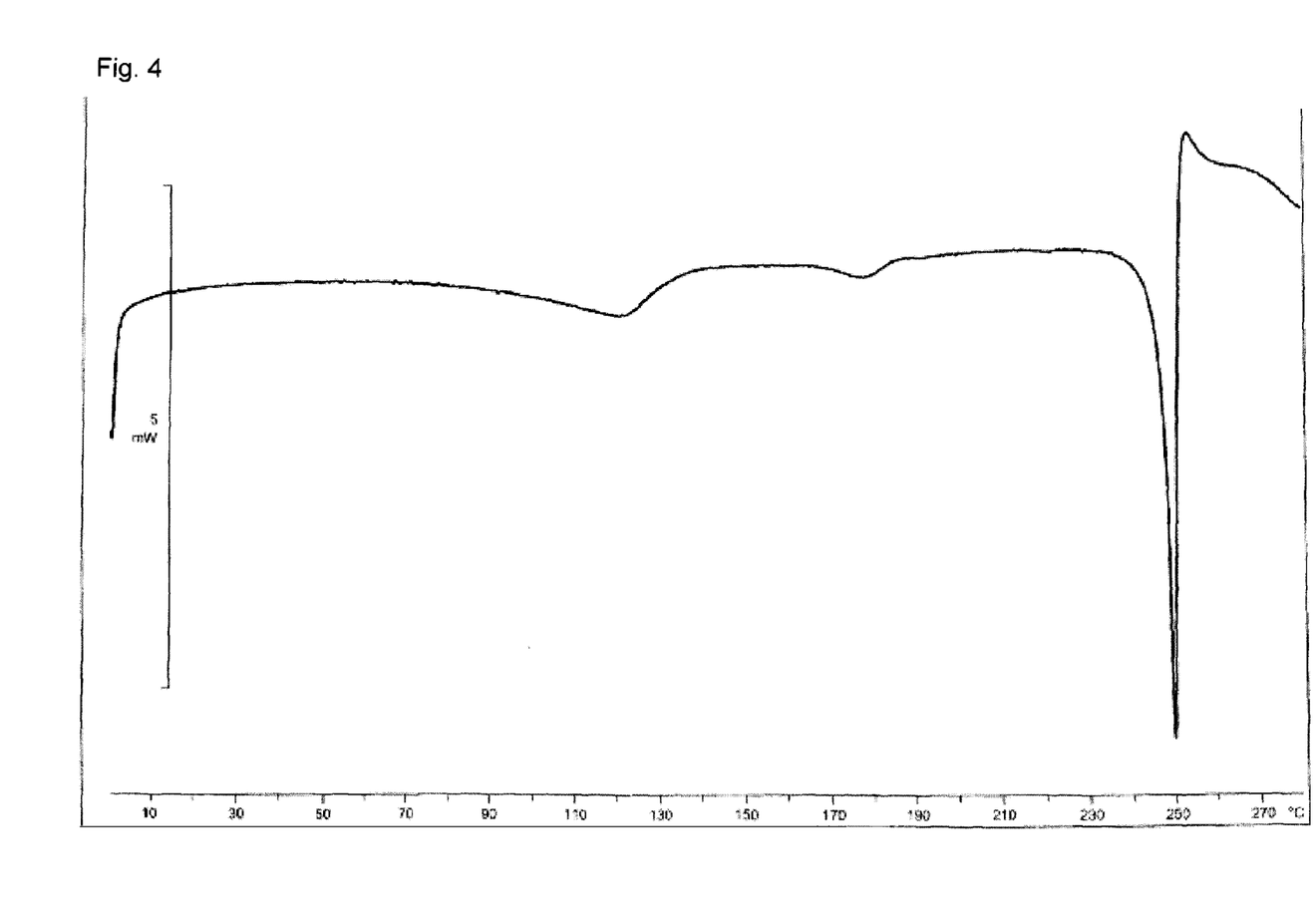
FIG. 4: is a differential scanning calorimetry (DSC) thermogram of APO-II.

In illustrative embodiments of the present invention, there is provided an APO-II polymorphic form of Lapatinib ditosylate described herein having a DSC thermogram substantially similar to a DSC thermogram as depicted in FIG. 4.

In illustrative embodiments of the present invention, there is provided a polymorphic form of Lapatinib ditosylate described herein in a pharmaceutical formulation.

In illustrative embodiments of the present invention, there is provided a process for preparing APO-I comprising: drying APO-II at atmospheric pressure.

In illustrative embodiments of the present invention, there is provided a process for preparing APO-I comprising drying APO-II in vacuo.

In illustrative embodiments of the present invention, there is provided a process described herein wherein the drying occurs at a temperature of from about 0° C. to about 60° C.

In illustrative embodiments of the present invention, there is provided a process described herein wherein the drying occurs at a temperature of from about 20° C. to about 50° C.

In illustrative embodiments of the present invention, there is provided a process for preparing APO-II comprising: I. mixing Lapatinib ditosylate with isopropanol thereby forming a first mixture; II. heating the first mixture to a first temperature; III. maintaining the first mixture at the first temperature; IV. cooling the first mixture to a second temperature; V. maintaining the first mixture at the second temperature thereby forming a first precipitate; and VI. recovering the first precipitate thereby isolating APO-II.

In illustrative embodiments of the present invention, there is provided a process for preparing APO-II comprising: I. mixing Lapatinib ditosylate with isopropanol thereby forming a second mixture; II. heating the second mixture to a third temperature; III. heating the second mixture to a fourth temperature; IV. maintaining the second mixture at the fourth temperature; V. cooling the second mixture to a fifth temperature; VI. maintaining the second mixture at the fifth temperature thereby forming a second precipitate; VII. recovering the second precipitate thereby isolating APO-II.

In illustrative embodiments of the present invention, there is provided a process described herein further comprising adding solid APO-II, APO-I, or a mixture thereof to the second mixture prior to heating the second mixture to the fourth temperature and after heating the second mixture to the third temperature.

In illustrative embodiments of the present invention, there is provided a process described herein wherein the Lapatinib ditosylate is selected from the group consisting of amorphous Lapatinib ditosylate, Lapatinib ditosylate monohydrate and mixtures thereof.

In illustrative embodiments of the present invention, there is provided a process for preparing APO-II comprising: I. mixing Lapatinib base with isopropanol thereby forming a third mixture; II. heating the third mixture to a sixth temperature; III. adding to the third mixture p-toluenesulfonic acid followed by isopropanol thereby forming a fourth mixture; IV. heating the fourth mixture to a seventh temperature; V. maintaining the fourth mixture at the seventh temperature; VI. cooling the fourth mixture to an eighth temperature; VII. maintaining the fourth mixture at the eighth temperature thereby forming a third precipitate; VIII. recovering the third precipitate thereby isolating APO-II.

In illustrative embodiments of the present invention, there is provided a process for preparing APO-II comprising: I. mixing Lapatinib base with isopropanol thereby forming a third mixture; II. heating the third mixture to a sixth temperature; III. adding to the third mixture an isopropanol solution of p-toluenesulfonic acid thereby forming a fourth mixture; IV. heating the fourth mixture to a seventh temperature; V. maintaining the fourth mixture at the seventh temperature; VI. cooling the fourth mixture to an eighth temperature; VII. maintaining the fourth mixture at the eighth temperature thereby forming a third precipitate; VIII. recovering the third precipitate thereby isolating APO-II.

In illustrative embodiments of the present invention, there is provided a process described herein further comprising adding solid APO-II, APO-I or a mixture thereof to the third mixture prior to adding p-toluenesulfonic acid and after heating the third mixture to the sixth temperature.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Drawings which illustrate embodiments of the invention are.

DETAILED DESCRIPTION

When used in reference to a diffractogram, a spectrum and/or data presented in a graph, the term "substantially similar" means that the subject diffractogram, spectrum and/or data presented in a graph encompasses all diffractograms, spectra and/or data presented in graphs that vary within acceptable boundaries of experimentation that are known to a person of skill in the art. Such boundaries of experimentation will vary depending on the type of the subject diffractogram; spectrum and/or data presented in a graph, and are known to and understood by a person of skill in the art.

When used in reference to a peak in a powder X-ray diffraction (PXRD) diffractogram, the term "approximately" means that the peak may vary by ±0.2 degrees 2θ of the subject value.

When used in reference to a peak in a differential scanning calorimetry (DSC) thermogram, the term "approximately" means that the peak may vary by ±1 degree of the subject value.

As used herein when referring to a diffractogram, spectrum and/or to data presented in a graph, the term "peak" refers to a feature that one skilled in the art would recognize as not attributing to background noise.

Depending on the nature of the methodology applied and the scale selected to display results obtained from an X-ray diffraction analysis, an intensity of a peak obtained may vary quite dramatically. For example, it is possible to obtain a relative peak intensity of 0.01% when analyzing one sample of a substance, but another sample of the same substance may show a much different relative intensity for a peak at the same position. This may be due, in part, to the preferred orientation of the sample and its deviation from the ideal random sample orientation, sample preparation and the methodology applied. Such variations are known and understood by a person of skill in the art.

In an illustrative embodiment, the present invention comprises a crystalline form of Lapatinib ditosylate which is a polymorphic form referred to herein as APO-I. A typical DSC thermogram for APO-I comprises two endothermic peaks with peak onset temperatures of approximately 169.5° C. and 247.9° C. and peak maximums of approximately 179.5° C. and 250.5° C. An illustrative DSC thermogram of APO-I is given in FIG. 2.

Illustrative peaks, expressed in angle 2-theta, appearing in a typical PXRD for APO-I include 4.6±0.2, 8.3±0.2, 9.3±0.2, 11.8±0.2, 13.8±0.2, 14.9±0.2, 16.8±0.2, 17.3±0.2, 18.8±0.2, 19.5±0.2, 21.3±0.2, 22.0±0.2, 23.0±0.2, 25.2±0.2, and 26.2±0.2. Illustrative relative peak intensities of the aforementioned peaks appearing in a typical PXRD for APO-I, expressed in terms of percent, are illustrated below in Table 1.

TABLE 1

| Relative Peak Intensities for APO-I | |
|---|---|
| Angle 2-theta | Relative Intensity % |
| 4.6 | 100.0 |
| 8.3 | 9.3 |
| 9.3 | 3.5 |
| 11.8 | 9.2 |
| 13.8 | 6.0 |
| 14.9 | 9.6 |
| 16.8 | 7.0 |
| 17.3 | 7.8 |
| 18.8 | 22.8 |
| 19.5 | 33.2 |
| 21.3 | 20.8 |
| 22.0 | 23.2 |
| 23.0 | 13.7 |
| 25.2 | 10.3 |
| 26.2 | 11.7 |

An illustrative PXRD diffractogram of APO-I is given in FIG. 1.

In an illustrative embodiment, the present invention comprises a crystalline isopropanol solvate form of Lapatinib ditosylate which is a polymorphic form referred to herein as APO-II. A typical DSC thermogram for APO-II comprises three endothermic peaks with peak onset temperatures of approximately 98.5° C., 167.7° C. and 247.0° C. and peak maximums of approximately 119.5° C., 177.8° C. and 249.4° C. An illustrative DSC thermogram of APO-II is given in FIG. 4.

Illustrative peaks, expressed in angle 2-theta, appearing in a typical PXRD for APO-I include 4.4±0.2, 8.3±0.2, 9.6±0.2, 10.5±0.2, 13.1±0.2, 14.0±0.2, 15.0±0.2, 16.9±0.2, 18.2±0.2, 19.3±0.2, 20.9±0.2, 21.4±0.2, 25.3±0.2, and 26.6±0.2. Illustrative relative peak intensities of the aforementioned peaks appearing in a typical PXRD for APO-II, expressed in terms of percent, are illustrated below in Table 2.

TABLE 2

| Relative Peak Intensities for APO-II | |
|---|---|
| Angle 2-theta | Relative Intensity % |
| 4.4 | 100.0 |
| 8.3 | 10.3 |
| 9.6 | 3.5 |
| 10.5 | 3.1 |
| 13.1 | 7.2 |

TABLE 2-continued

| Relative Peak Intensities for APO-II | |
|---|---|
| Angle 2-theta | Relative Intensity % |
| 14.0 | 3.3 |
| 15.0 | 2.7 |
| 16.9 | 4.6 |
| 18.2 | 6.2 |
| 19.3 | 12.8 |
| 20.9 | 21.5 |
| 21.4 | 15.0 |
| 25.3 | 7.6 |
| 26.6 | 7.2 |

An illustrative PXRD diffractogram of APO-II is given in FIG. 3.

In another illustrative embodiment, the present invention provides a process of preparing APO-II comprising:
 a. mixing Lapatinib ditosylate with isopropanol thereby forming a first mixture;
 b. heating the first mixture to a first temperature;
 c. maintaining the first mixture at the first temperature;
 d. cooling the first mixture to a second temperature;
 e. maintaining the first mixture at the second temperature thereby forming a first precipitate; and
 f. recovering the first precipitate thereby isolating APO-II.

The Lapatinib ditosylate for mixing with isopropanol may be in any form or a mixture of forms, for example and without limitation, amorphous Lapatinib ditosylate and/or Lapatinib ditosylate monohydrate.

A volume of isopropanol used to mix with the Lapatinib ditosylate may be from about 5 volumes to about 20 volumes. The volume may be from about 6 volumes to about 10 volumes.

The first temperature may be in a range of from about 60° C. to about 82° C. The first temperature may be approximately refluxing temperature. The first mixture is maintained at the first temperature for a first period of time from about 0.5 hours to about 18 hours. Often the first period of time is from about 2 hours to about 8 hours. Often the first period of time is from about 4 hours to about 5 hours.

The second temperature may be in a range of from about 0° C. to about 40° C. The second temperature may be in a range of from about 20° C. to about 30° C. The first mixture is maintained at the second temperature for a second period of time from about 0.5 hours to about 18 hours. Often the second period of time is from about 2 hours to about 5 hours.

Recovering the first precipitate may be carried out by any known method such as filtration, centrifugation, and/or decantation.

In another illustrative embodiment, the present invention provides another process of preparing APO-II comprising:
 g. mixing Lapatinib ditosylate with isopropanol thereby forming a second mixture;
 h. heating the second mixture to a third temperature;
 i. optionally adding solid APO-II, APO-I or both to the second mixture;
 j. heating the second mixture to a fourth temperature;
 k. maintaining the second mixture at the fourth temperature;
 l. cooling the second mixture to a fifth temperature;
 m. maintaining the second mixture at the fifth temperature thereby forming a second precipitate; and
 n. recovering the second precipitate thereby isolating APO-II.

The Lapatinib ditosylate for mixing with isopropanol may be in any form or a mixture of forms, for example and without limitation, amorphous Lapatinib ditosylate and/or Lapatinib ditosylate monohydrate.

A volume of isopropanol used to mix with the Lapatinib ditosylate may be from about 5 volumes to about 20 volumes. The volume may be from about 6 volumes to about 10 volumes.

The third temperature may be in a range of from about 55° C. to about 75° C. The third temperature may be in a range of from about 60° C. to about 65° C.

If added, an amount of APO-II, APO-I or both used in step i may be from about 0.01 w/w percent to about 50 w/w percent relative to the amount of Lapatinib ditosylate added in step g. Hence, the second mixture may or may not contain one or both of added APO-I and/or APO-II The fourth temperature may be in a range of from about 60° C. to about 82° C. The fourth temperature may be approximately refluxing temperature. The second mixture is maintained at the fourth temperature for a third period of time from about 0.5 hours to about 18 hours. The third period of time may be from about 2 hours to about 8 hours. Often the third period of time is about 4 hours to about 5 hours.

The fifth temperature may be in a range of from about 0° C. to about 40° C. The fifth temperature may be from about 20° C. to about 30° C. The second mixture is maintained at the fifth temperature for a fourth period of time from about 0.5 hours to about 18 hours. Often the fourth period of time is from about 2 hours to about 5 hours.

Recovering the second precipitate may be carried out by any known method such as filtration, centrifugation, and/or decantation.

In another illustrative embodiment, the present invention provides another process of preparing APO-II comprising:
o. mixing Lapatinib base with isopropanol thereby forming a third mixture;
p. heating the third mixture to a sixth temperature;
q. optionally adding solid APO-II, APO-I or both to the third mixture;
r. adding to the third mixture p-toluenesulfonic acid followed by isopropanol or adding an isopropanol solution of p-toluenesulfonic acid thereby forming a fourth mixture;
s. heating the fourth mixture to a seventh temperature;
t. maintaining the fourth mixture at the seventh temperature;
u. cooling the fourth mixture to an eighth temperature;
v. maintaining the fourth mixture at the eighth temperature thereby forming a third precipitate; and
w. recovering the third precipitate thereby isolating APO-II.

A volume of isopropanol used to mix with the Lapatinib base may be from about 5 volumes to about 20 volumes. The volume may be from about 6 volumes to about 10 volumes.

The sixth temperature may be in a range of from about 55° C. to about 75° C. The sixth temperature may be in a range of from about 65° C. to about 75° C.

If added, an amount of APO-II, APO-I or both used in step q may be from about 0.01 w/w percent to about 50 w/w percent relative to the amount of Lapatinib added in step o. Hence, the third mixture may or may not contain one or both of added APO-I and/or APO-II. Similarly, depending on whether or not one or both of APO-I and/or APO-II was added to the third mixture, the composition of the fourth mixture will vary accordingly.

An amount of p-toluenesulfonic acid (whether in an isopropanol solution or not) added to the third mixture is about 2.0 equivalents to about 2.2 equivalents.

The seventh temperature may be in a range of from about 60° C. to about 82° C. The seventh temperature may be approximately refluxing temperature. The fourth mixture is maintained at the seventh temperature for a fifth period of time from about 0.5 hours to about 18 hours. Often the fifth period of time is from about 2 hours to about 8 hours. Often the fifth period of time is from about 4 hours to about 5 hours.

The eighth temperature may be in a range of from about 0° C. to about 40° C. The eighth temperature may be from about 20° C. to about 30° C. The fourth mixture is maintained at the eighth temperature for a sixth period of time from about 0.5 hours to about 18 hours. Often the sixth period of time is from about 2 hours to about 5 hours.

Recovering the third precipitate may be carried out by any known method such as filtration, centrifugation, and/or decantation.

Following the above steps a-f and/or g-n and/or o-w, polymorphic Form APO-II Lapatinib ditosylate may be produced.

In another illustrative embodiment, the present invention provides a process of preparing APO-I comprising drying APO-II at atmospheric pressure or in vacuo. The drying may occur at a temperature in a range of from about 0° C. to about 60° C. The drying temperature may be in the range of from about 20° C. to about 50° C. Often the drying temperature may be in a range of from about 45° C. to about 50° C.

The following examples are illustrative of some of the embodiments of the invention described herein. These examples do not limit the spirit or scope of the invention in anyway.

EXAMPLES

Powder X-Ray Diffraction (PXRD) Analysis: The data were acquired on a PANanalytical X-Pert Pro MPD diffractometer with fixed divergence slits and an X-Celerator RTMS detector. The diffractometer was configured in Bragg-Brentano geometry; data was collected over a 2 theta range of 3 to 40 using CuKa radiation at a power of 40 mA and 45 kV. CuK$\beta$ radiation was removed using a divergent beam nickel filter. A step size of 0.017 degrees was used. A step time of 50 seconds was used. Samples were rotated at 1 Hz to reduce preferred orientation effects. The samples were prepared by the back-loading technique.

Differential Scanning Calorimetry (DSC) Analysis: The DSC thermograms were collected on a Mettler-Toledo 821e instrument. Samples (1 to 3 mg) were weighed into a 40 μL aluminum pan and were crimped closed with an aluminum lid. The samples were analyzed under a flow of nitrogen (ca. 55 mL/min) at a scan rate of 10° C./minute, from 0 to 280° C.

Example 1

Preparation of Isopropanol Solvate of Lapatinib Ditosylate (APO-II) and APO-I Form of Lapatinib Ditosylate Lapatinib ditosylate monohydrate (15 g) was slurried in isopropyl alcohol (90 mL) at 80-82° C. for about 4 h. The mixture was cooled down slowly to 20-25° C. and stirred at that temperature for about 16 h, filtered, washed with isopropyl alcohol (38 mL) and suction dried to provide Lapatinib ditosylate isopropanol solvate (APO-II). The APO-II product obtained was subjected to PXRD analysis and the results are shown in FIG. 3. DSC analysis was also performed and the results obtained were substantially similar to those shown in FIG. 4.

Lapatinib ditosylate isopropanol solvate from above was dried in vacuo at 45-50° C. for 82 hours to provide 13.7 g of Lapatinib ditosylate of crystalline form APO-I. The APO-I product obtained was subjected to PXRD analysis as well as DSC analysis and the results are shown in FIGS. 1 and 2, respectively.

Example 2

Preparation of isopropanol solvate of Lapatinib ditosylate (APO-II) and APO-I Form of Lapatinib Ditosylate Using Seeding A mixture of Lapatinib ditosylate monohydrate (10 g) and isopropyl alcohol (60 mL) was heated to 60-65° C., seeded with crystals of Lapatinib ditosylate form APO-I (0.8 g) and the suspension heated to 80-82° C. and slurried for about 4 h. The mixture was cooled down slowly to 25-30° C., filtered, washed with isopropyl alcohol (25 mL) and suction dried to provide Lapatinib ditosylate isopropanol solvate (APO-II). The APO-II product obtained was subjected to PXRD analysis as well as DSC analysis. The results of the PXRD analysis and the DSC analysis were substantially similar to those shown in FIGS. 3 and 4.

Lapatinib ditosylate isopropanol solvate from above was dried in vacuo at 45-50° C. for 1 day to provide 10.2 g of Lapatinib ditosylate crystalline form APO-I. The APO-I product obtained was subjected to PXRD analysis as well as DSC analysis. The results of the PXRD analysis were substantially similar to those shown in FIG. 1.

Example 3

Preparation of Isopropanol Solvate of Lapatinib Ditosylate (APO-II) and APO-I Form of Lapatinib Ditosylate from Lapatinib Base A mixture of Lapatinib base (2 g) and isopropyl alcohol (18 mL) were heated to 70-75° C. Seeds of Lapatinib ditosylate form APO-I (0.1 g) were added, followed by p-toluenesulfonic acid monohydrate (1.37 g, 2.1 eq.), and rinsed with isopropanol (2 mL). The suspension was heated to 80-82° C. for about 4 h. The mixture was cooled down slowly to 25-30° C., filtered, washed with isopropanol (5 mL) and suction dried to provide Lapatinib ditosylate isopropanol solvate (APO-II). The APO-II product obtained was subjected to PXRD analysis. The results of the PXRD analysis were substantially similar to those shown in FIG. 3.

Lapatinib ditosylate isopropanol solvate from above was dried in vacuo at 45-50° C. for about 1 day to provide 3.0 g of Lapatinib ditosylate form APO-I. The APO-I product formed was subjected to PXRD analysis. The results of the PXRD analysis were substantially similar to those shown in FIG. 1.

Example 4

Preparation of Isopropanol Solvate of Lapatinib Ditosylate (APO-II)

Amorphous Lapatinib ditosylate (1 g—prepared according to methods similar to those described in example 1 of WO 2009/079541) in isopropyl alcohol (6 mL) was heated to about 75° C. Additional isopropyl alcohol (1 mL) was added and the mixture was slurried at that temperature for about 4 h.

The mixture was cooled down slowly to 20-25° C. and stirred at that temperature for about 18 h, filtered, washed with isopropyl alcohol and suction dried to provide Lapatinib ditosylate isopropanol solvate (APO-II). The APO-II product formed was subjected to PXRD analysis as well as DSC analysis. The results of the PXRD analysis were substantially similar to those shown in FIG. 3. The results of the DSC analysis are shown in FIG. 4.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. Furthermore, numeric ranges are provided so that the range of values is recited in addition to the individual values within the recited range being specifically recited in the absence of the range. The word "comprising" is used herein as an open-ended term, substantially equivalent to the phrase "including, but not limited to", and the word "comprises" has a corresponding meaning. As used herein, the singular forms "a", "an" and "the" include plural references unless the context clearly dictates otherwise. Thus, for example, reference to "a thing" includes more than one such thing. Citation of references herein is not an admission that such references are prior art to the present invention. Furthermore, material appearing in the background section of the specification is not an admission that such material is prior art to the invention. Any priority document(s) are incorporated herein by reference as if each individual priority document were specifically and individually indicated to be incorporated by reference herein and as though fully set forth herein. The invention includes all embodiments and variations substantially as hereinbefore described and with reference to the examples and drawings.

What is claimed is:

1. APO-I polymorphic form of Lapatinib ditosylate having a powder X-ray diffraction pattern comprising peaks, in terms of degrees 2-theta, at approximately 4.6, 8.3, 18.8, 19.5, 21.3, 22.0 and 23.0.

2. The APO-I polymorphic form of Lapatinib ditosylate of claim 1 wherein the powder X-ray diffraction pattern further comprises peaks, in terms of degrees 2-theta, at approximately 9.3, 11.8, 13.8, 14.9, 16.8, 17.3, 25.2 and 26.2.

3. The APO-I polymorphic form of Lapatinib ditosylate of claim 2 having a DSC thermogram comprising two endothermic peaks with peak onset temperatures of approximately 169.5° C. and 247.9° C. and peak maximums of approximately 179.5° C. and 250.5° C.

4. The APO-I polymorphic form of Lapatinib ditosylate of claim 1 having a PXRD diffractogram as depicted in FIG. 1.

5. The APO-I polymorphic form of Lapatinib ditosylate of claim 2 having a DSC thermogram as depicted in FIG. 2.

6. APO-II polymorphic form of Lapatinib ditosylate having a powder X-ray diffraction pattern comprising peaks, in terms of degrees 2-theta, at approximately 4.4, 8.3, 13.1, 14.0, 19.3, 20.9 and 21.4.

7. The APO-II polymorphic form of Lapatinib ditosylate of claim 6 wherein the powder X-ray diffraction pattern further comprises peaks, in terms of degrees 2-theta, at approximately 9.6, 10.5, 15.0 16.9, 18.2, 25.3, and 26.6.

8. The APO-II polymorphic form of Lapatinib ditosylate of claim 7 having a DSC thermogram comprising three endothermic peaks with peak onset temperatures of approximately 98.5° C., 167.7° C. and 247.0° C. and peak maximums of approximately 119.5° C., 177.8° C. and 249.4° C.

9. The APO-II polymorphic form of Lapatinib ditosylate of claim 6 having a PXRD diffractogram as depicted in FIG. 3.

10. The APO-II polymorphic form of Lapatinib ditosylate of claim 7 having a DSC thermogram as depicted in FIG. 4.

11. The polymorphic form of claim 1 in a pharmaceutical formulation.

12. A process for preparing APO-I comprising: drying APO-II at atmospheric pressure.

13. A process for preparing APO-I comprising drying APO-II in vacuo.

14. The process of claim 12 wherein the drying occurs at a temperature of from 0° C. to 60° C.

15. The process of claim 12 wherein the drying occurs at a temperature of from 20° C. to 50° C.

16. A process for preparing APO-II comprising:
   I. mixing isopropanol with Lapatinib ditosylate selected from the group consisting of amorphous Lapatinib ditosylate, Lapatinib ditosylate monohydrate and mixtures thereof thereby forming a first mixture;
   II. heating the first mixture to a first temperature;
   III. maintaining the first mixture at the first temperature;
   IV. cooling the first mixture to a second temperature;
   V. maintaining the first mixture at the second temperature thereby forming a first precipitate; and
   VI. recovering the first precipitate thereby isolating APO-II.

17. A process for preparing APO-II comprising:
   I. mixing Lapatinib ditosylate with isopropanol thereby forming a second mixture;
   II. heating the second mixture to a third temperature;
   III. heating the second mixture to a fourth temperature;
   IV. maintaining the second mixture at the fourth temperature;
   V. cooling the second mixture to a fifth temperature;
   VI. maintaining the second mixture at the fifth temperature thereby forming a second precipitate;
   VII. recovering the second precipitate thereby isolating APO-II.

18. The process of claim 17 further comprising adding solid APO-II, APO-I, or a mixture thereof to the second mixture prior to heating the second mixture to the fourth temperature and after heating the second mixture to the third temperature.

19. A process for preparing APO-II comprising:
   I. mixing Lapatinib base with isopropanol thereby forming a third mixture;
   II. heating the third mixture to a sixth temperature;
   III. adding to the third mixture p-toluenesulfonic acid followed by isopropanol thereby forming a fourth mixture;
   IV. heating the fourth mixture to a seventh temperature;
   V. maintaining the fourth mixture at the seventh temperature;
   VI. cooling the fourth mixture to an eighth temperature;
   VII. maintaining the fourth mixture at the eighth temperature thereby forming a third precipitate;
   VIII. recovering the third precipitate thereby isolating APO-II.

20. A process for preparing APO-II comprising:
   I. mixing Lapatinib base with isopropanol thereby forming a third mixture;
   II. heating the third mixture to a sixth temperature;
   III. adding to the third mixture an isopropanol solution of p-toluenesulfonic acid thereby forming a fourth mixture;
   IV. heating the fourth mixture to a seventh temperature;
   V. maintaining the fourth mixture at the seventh temperature;
   VI. cooling the fourth mixture to an eighth temperature;
   VII. maintaining the fourth mixture at the eighth temperature thereby forming a third precipitate;
   VIII. recovering the third precipitate thereby isolating APO-II.

21. The process of claim 19 further comprising adding solid APO-II, APO-I or a mixture thereof to the third mixture prior to adding p-toluenesulfonic acid and after heating the third mixture to the sixth temperature.

22. The polymorphic form of claim 6 in a pharmaceutical formulation.

23. The process of claim 17 wherein the Lapatinib ditosylate is selected from the group consisting of amorphous Lapatinib ditosylate, Lapatinib ditosylate monohydrate and mixtures thereof.

24. The process of claim 20 further comprising adding solid APO-II, APO-I or a mixture thereof to the third mixture prior to adding p-toluenesulfonic acid and after heating the third mixture to the sixth temperature.

* * * * *